United States Patent [19]

Bellingham et al.

[11] Patent Number: 4,881,037

[45] Date of Patent: Nov. 14, 1989

[54] APPARATUS AND METHOD FOR MEASURING THE INTERFACIAL IMPEDANCE IN AN ELECTROCHEMICAL CELL

[75] Inventors: James G. Bellingham, West Harwich, Mass.; Margaret L. A. MacVicar, West Lebanon, Me.

[73] Assignee: Massachusetts Institute of Technology, Cambridge, Mass.

[21] Appl. No.: 302,420

[22] Filed: Jan. 26, 1989

[51] Int. Cl.$^4$ ............................................. G01N 27/00
[52] U.S. Cl. ................................. 324/425; 324/77 B; 324/348; 204/404
[58] Field of Search .............. 204/404, 400; 324/77 B, 324/444, 445, 446, 65 R, 348, 376, 439

[56] References Cited

U.S. PATENT DOCUMENTS 3,947,329  3/1976  Seyl ...................................... 324/444
4,575,678  3/1986  Hladky .

OTHER PUBLICATIONS

Haruyama et al., "A Corrosion Monitor Based on Impedance Method," *Electrochemical Corrosion Testing*, ASTM STP 727, pp. 167–186 (1981).
Bellingham et al., *J. Electrochem. Soc.* 133: 1753–1754 (1986).
Bellingham et al., *IEEE Trans. on Magnetics* MAG-23, pp. 477–479 (3/87).
Murphy et al., *J. Electrochem. Soc.* 135:310–313 (2/88).
Sarwinski, "Superconducting Instruments" in *Cryogenics*, pp. 671–679 (1977).
Clarke et al., *Science* 242:217 (10/14/88).
Moulder et al., *J. Res. Nat'l Bureau of Stds.*, vol. 92 pp. 27–33 (Jan.–Feb. 1987).
Bain et al., *IEEE Transactions on Magnetics* MAG-23, pp. 473–476 (3/87).
Weinstock et al. 3rd Int'l Conf. on Superconducting Quantum Devices (1985).
Clarke, "Overview of Applications of SQUIDS," in Proc. of SQUID Magnetometry Workshop, pp. 3–7 (1984).
Bellingham et al., "Electrochemical Noise Mechanisms in the Dissolution of Zn in HCl" (1988).
Bellingham et al., "Characterization of Electrochemical Reactions Using a Superconducting Magnetometer" (1988).

*Primary Examiner*—Reinhard J. Eisenzopf
*Assistant Examiner*—Jose M. Solis
*Attorney, Agent, or Firm*—Fish & Richardson

[57] ABSTRACT

Apparatus for measuring the interfacial impedance in an electrochemical cell having a pair of electrodes in contact with an electrolyte medium that includes circuitry for measuring the interaction current flowing between the electrodes at a series of predetermined external impedance values and an analyzer for determining the interfacial impedance based on the current measurements.

10 Claims, 2 Drawing Sheets

APPARATUS AND METHOD FOR MEASURING THE INTERFACIAL IMPEDANCE IN AN ELECTROCHEMICAL CELL

This invention was made with U.S. government support under Sea Grant Contract No. NA86AA-D-S6089 and ONR Contract No. N00014-85-K-0754, and the U.S. government has rights in this invention.

BACKGROUND OF THE INVENTION

This invention relates to measuring impedance at an electrochemical interface.

Electrochemical corrosion is a costly problem for many metal structures. In electrochemical corrosion, a bulk metal reacts with an electrolyte, resulting in loss of metal from the bulk. Metal atoms are removed from the bulk metal by an oxidation reaction at the interface, resulting in a net current flowing into the electrolyte. A reduction reaction balances the charge transfer process, generating a current equal in magnitude to the oxidation current but of opposite polarity.

The rate of corrosion is known to be related to the charge transfer resistance at the interface of the oxidizing metal surface and electrolyte. The charge transfer resistance is a measure on the difficulty in moving charged species across the interface between the metal and the electrolyte. Since metal atoms are removed from the bulk as charged species, the charge transfer resistance indicates the ease with which corrosion can proceed. It can be determined by measuring the impedance at the metal-electrolyte interface. Typically, this is accomplished by applying an external voltage or current across an electrochemical cell having a pair of metal electrodes immersed in a liquid electrolyte and measuring the response of the cell, from which the interfacial impedance is calculated.

SUMMARY OF THE INVENTION

In general, the invention features apparatus for measuring the interfacial impedance in an electrochemical cell having a pair of electrodes in contact with an electrolyte medium that includes circuitry for measuring the interaction current flowing between the electrodes at a series of predetermined external impedance values and an analyzer for determining the interfacial impedance based on the interaction current measurements. The interaction current is the current that inherently flows between the electrodes as a result of the oxidation and reduction reactions taking place at the electrode surfaces even in the absence of an externally applied current or voltage. The external impedance refers to an impedance in the circuit external to the electrochemical cell.

In preferred embodiments, the circuitry for measuring the interaction current includes a variable impedance element for establishing the predetermined external impedance values and either a low impedance ammeter for detecting the interaction current directly or a voltmeter for measuring the voltage drop across the variable impedance element to determine the interaction current indirectly (through application of Ohm's Law). The preferred ammeter is a magnetometer, e.g., a superconducting quantum interference device magnetometer and the preferred variable impedance element is a variable resistor. The preferred analyzer is a digital computer.

The interfacial impedance is measured by determining the interaction current flowing between the electrodes as a function of frequency at a series of predetermined external impedance values and then determining the interfacial impedance based o the interaction current. Preferably, the interaction current is measured over a set of predetermined time intervals for each predetermined external impedance value to obtain the interaction current as a function of time and external impedance. The time-dependent interaction current values are then transformed to yield the interaction current as a function of frequency and external impedance.

The invention also features a method for determining the source of the interaction current by determining the interaction current flowing between the electrodes as a function of frequency at a series of predetermined external impedance values and comparing the resulting interaction current function with a set of interaction current functions corresponding to known sources to determine the desired source.

The invention provides a simple and accurate way for determining interfacial impedance. There is no need for an externally applied current or voltage source. Corrosion resistance can be determined from the interfacial impedance, thereby enabling preventive measures to be taken. The ability to determine the source of the interaction current is useful, e.g., in designing corrosion-resistant metals, increasing the efficiency of electrochemical processes, and predicting the onset of catastrophic corrosion processes (e.g., pitting).

Other features and advantages of the invention will be apparent from the following description of the preferred embodiments thereof and from the claims.

DESCRIPTION OF THE PREFERRED EMBODIMENTS

We first briefly describe the drawings.

STRUCTURE

Figure 1:
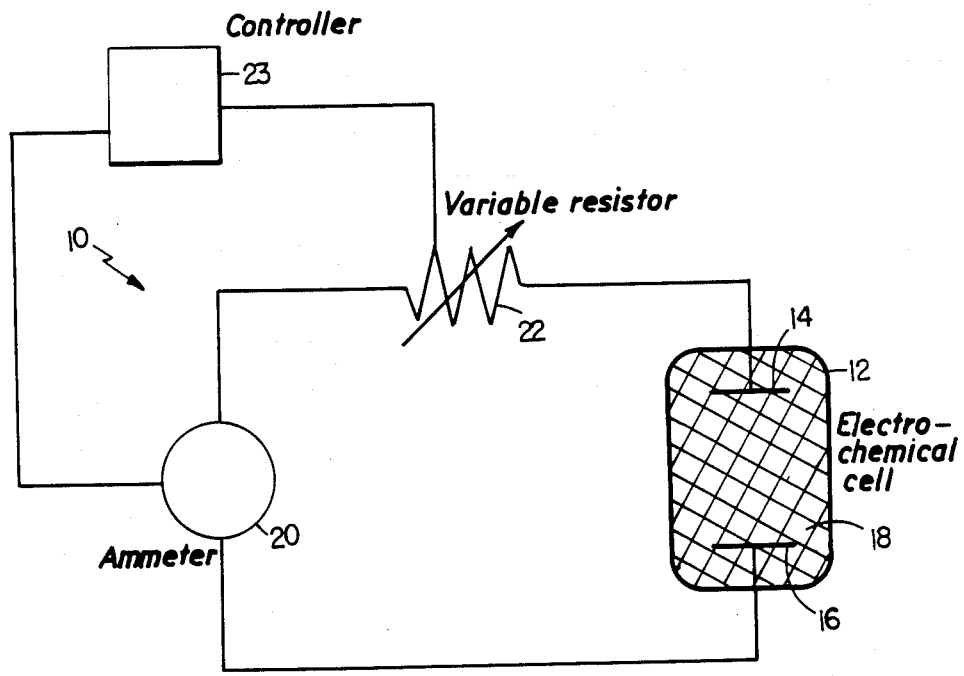
FIGS. 1 and 2 are schematic drawings of electrical circuits for measuring the interaction current in an electrochemical cell.

There is shown in FIG. 1 an electrical circuit 10 for measuring the interaction current in an electrochemical cell 12. Cell 12 contains two opposing metal electrodes 14 and 16 immersed in a liquid electrolyte 18.

The materials for electrodes 14 and 16 are metals whose corrosion resistance is of interest. Typical metals include zinc, aluminum, and tin. Electrolyte 18 is chosen to simulate a desired corrosive environment. It is typically an aqueous solution of acid or a salt, e.g., hydrochloric acid or sodium chloride.

Even in the absence of an externally applied current or voltage, there is an inherent flow of current between electrodes 14 and 16. This current flow is called the interaction current, although it is sometimes referred to as noise current to reflect the fact that it is produced by stochastic processes. Sources of the interaction current generally fall into several categories. One category includes the current generated by fluctuations in the rate of chemical reactions at the electrode/electrolyte interface. Falling within this category would be fluctuations in corrosion rate due to the emergence of defects (e.g., pits) in the receding surface. Another category includes current generated by changes in the conductivity of electrolyte 18 as a result of interfacial chemical reactions. In this second category would be the conductivity change due to hydrogen bubble evolution.

The electrode/electrolyte interface can be modeled as a parallel plate capacitor connected in parallel with an impedance element. The capacitor reflects the fact that there is a double layer of charge in the vicinity of the electrode surface and interface. The impedance element reflects the opposition of the interface to the transfer of metal ions (i.e. the interfacial impedance). In turn, both of the above-described sources of the interaction current can be modeled as either a voltage or current source in parallel with the circuit used to model the interface. This gives rise to the following four sets of equations for measurements made at low frequency that characterize the interaction current from which the interfacial impedance can be determined; in any particular electrochemical cell, the interaction current will be described mostly closely by one of these four equations:

$$S_m(\omega) = S_I(\omega) \left| \frac{Z(\omega)}{2Z(\omega) + R_t} \right|^2 \quad (1)$$

chemical reaction rate change - current source $$S_m(\omega) = S_V(\omega) \left| \frac{1}{Z(\omega) + R_t} \right|^2 \quad (2)$$

chemical reaction rate change - voltage source $$S_m(\omega) = S_R(\omega) \left| \frac{i_o Z(\omega)}{(2Z(\omega) + R_t)^2} \right|^2 \quad (3)$$

cell conductivity change - current source $$S_m(\omega) = S_R(\omega) \left| \frac{V_o}{(Z(\omega) + R_t)^2} \right|^2 \quad (4)$$

cell conductivity change - voltage source cell conductivity change- voltage source where $S_m(\omega)$ is the detected interaction current power at frequency $\omega$;

$Z(\omega)$ is the interfacial impedance;

$R_t$ is the sum of the electrolyte resistance and the resistance value set by variable resistor 22;

$S_I(\omega)$ is the current source power;

$S_V(\omega)$ is the voltage source power;

$S_R(\omega)$ is the conductivity source power;

$i_o$ is a constant current in parallel with one of the interfaces; and $V_o$ is a constant voltage in parallel with one of the interfaces.

Figure 3:
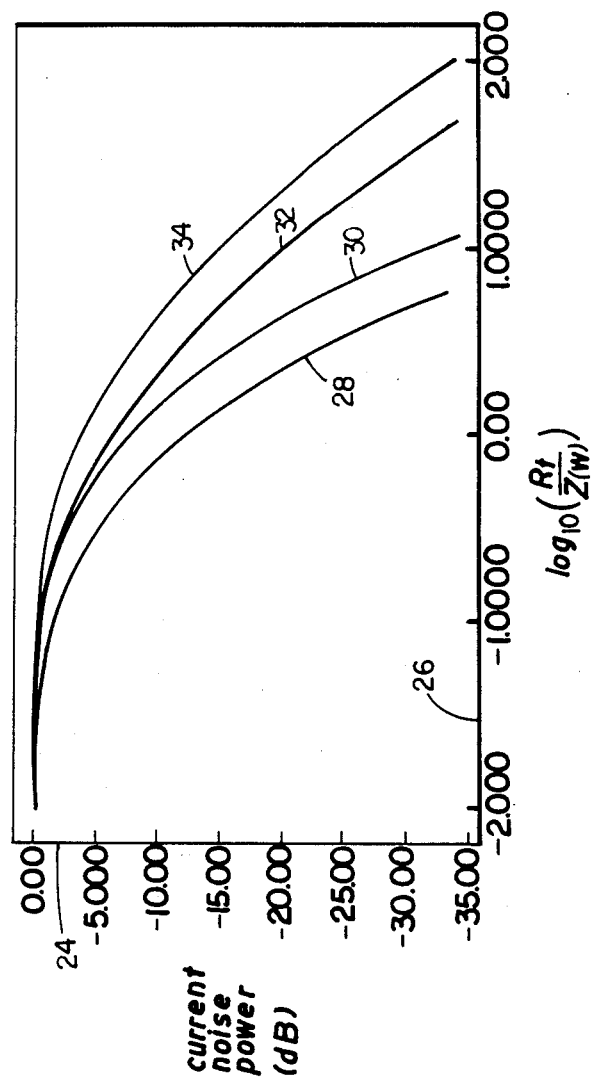
FIG. 3 is a graph showing the relationship between applied external impedance and the detected interaction current power.

Equations (1)-(4) are represented graphically in FIG. 3 in which x-axis 26 represents the base 10-logarithm of the ratio of the total external impedance ($R_t$) to the interfacial impedance ($Z(\omega)$), and y-axis 24 is the detected interaction current power ($S_m(\omega)$). Curve 28 corresponds to equation (4), curve 30 to equation (3), curve 32 to equation (2), and curve 34 to equation (1).

An ammeter 20 for detecting the interaction current through electrochemical cell 12 is connected in series with cell 12 and resistor 22. Ammeter 20 is a magnetometer. It detects the magnetic field associated with the interaction current. Because the magnetic field is proportional to the interaction current, a value for the interaction current is readily obtained. The advantage of the magnetometer is that it provides a non invasive means for measuring the interaction current. One type of suitable magnetometer is a superconducting quantum interference device (SQUID) magnetometer.

A controller 23 sets the values for resistor 22 and records and stores the interaction current data detected by ammeter 20. It also analyzes the data to obtain the interfacial impedance as described below. Controller 23 is preferably a digital computer, e.g., an IBM personal computer (PC).

Figure 2:
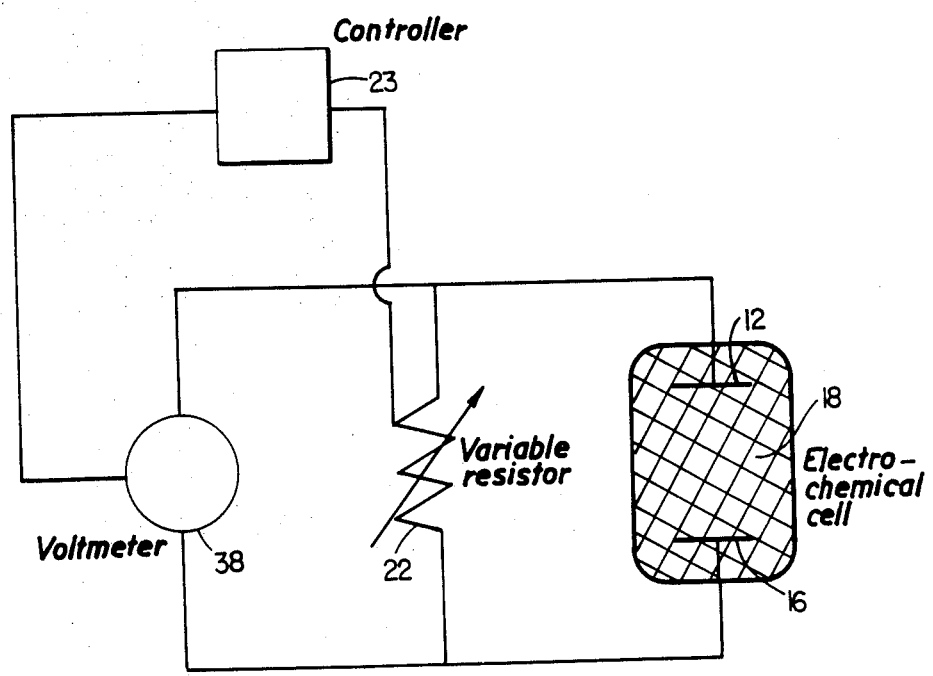

FIG. 2 shows a second electrical circuit 36 for measuring the interaction current in electrochemical cell 12. Circuit 36 includes a voltmeter 38 connected in parallel with cell 12 and resistor 22. The interaction current is measured by recording the voltage drop across resistor 22 and calculating the current using Ohm's Law [i.e. current (i)=voltage (V)/resistance (R)].

OPERATION

The interfacial impedance of cell 12 is determined as follows.

A value for resistor 22 is chosen by controller 23 and the interfacial current flowing between electrodes 14 and 16 is measured at ammeter 20 over a series of time intervals at this resistance; a typical time interval is about 60 seconds. The resistance of resistor 22 is then changed and another set of interaction current measurements over time obtained. This procedure is repeated until a sufficient number of measurements has been taken; the greater the number of measurements, the more accurate the interfacial impedance will be. The data are stored in controller 23.

From the time dependent interaction current measurements at a series of external resistance values, controller 23 obtains the power spectrum to yield the interaction current power $S_m(\omega)$ as a function of the external resistance as set by resistor 22. The external resistance is then modified to include resistance due to the electrolyte to give the interaction current power as a function of total external resistance ($R_t$). The electrolyte resistance is measured directly or calculated from the cell geometry and resistivity of the electrolyte.

If the source of the interaction current is known beforehand (i.e. if it is known which of the four mechanisms corresponding to equations (1)-(4), above, applies), controller 23 determines the value of the interfacial impedance by applying the measured data to the appropriate curve in FIG. 3, On the other hand, if the source is not known, a current source is assumed and the data are plotted to see which of the curves 30 and 34 in FIG. 3 most accurately describes it. The interfacial impedance is then determined by reference to the appropriate curve.

The charge transfer resistance can be determined from the interfacial impedance using known methods, e.g., as described in Haruyama et al., "A Corrosion Monitor Based On Impedance Method," *Electrochemical Corrosion Testing*, ASTM STP 727, F. Mansfield and U. Bertocci, eds., American Society for Testing and Materials, pp. 167-86 (1981). The simplest way is to take the highest value of the interfacial impedance and set it equal to the charge transfer resistance.

The charge transfer resistance is known to be inversely proportional to the tendency to corrode. Thus, the tendency to corrode can be readily obtained from the charge transfer resistance.

Other embodiments are within the following claims.

We claim:

1. Apparatus for measuring the interfacial impedance in an electrochemical cell having a pair of electrodes in contact with an electrolyte medium comprising
   circuitry for measuring the interaction current flowing between said electrodes at a series of predetermined external impedance values; and
   an analyzer for determining said interfacial impedance based on said current measurements.

2. The apparatus of claim 1 wherein said circuitry for measuring said current comprises an ammeter for detecting said interaction current and a variable impedance element for establishing said predetermined external impedance values.

3. The apparatus of claim 1 wherein said circuitry for measuring said current comprises a variable impedance element for establishing said predetermined external impedance values and a voltmeter for measuring the voltage drop across said variable impedance element to determine said interaction current.

4. The apparatus of claim 1 wherein said ammeter comprises a magnetometer.

5. The apparatus of claim 4 wherein said ammeter comprises a superconducting quantum interference device magnetometer.

6. The apparatus of claims 2 or 3 wherein said variable impedance element comprises a variable resistor.

7. The apparatus of claim 1 wherein said analyzer comprises a digital computer.

8. A method for measuring the interfacial impedance in an electrochemical cell having a pair of electrodes in contact with an electrolyte medium comprising the steps of
   determining the intrinsic interaction current flowing between said electrodes as a function of frequency at a series of predetermined external impedance values; and
   determining said interfacial impedance based on said interaction current.

9. The method of claim 8 wherein said interaction current is measured over a set of predetermined time intervals for each of said predetermined external impedance values to obtain said interaction current as a function of time and external impedance,
   whereupon said time-dependent interaction current values are transformed to yield said interaction current as a function of frequency and external impedance.

10. A method for determining the source of the intrinsic interaction current in an electrochemical cell having a pair of electrodes in contact with an electrolyte medium comprising the steps of
    determining the intrinsic interaction current flowing between said electrodes as a function of frequency at a series of predetermined external impedance values; and
    comparing said interaction current function with a set of interaction current functions corresponding to known sources to determine said source.

* * * * *